United States Patent [19]

Ude et al.

[11] Patent Number: 4,698,448

[45] Date of Patent: Oct. 6, 1987

[54] METHOD FOR MAKING AROMATIC PHOSPHORUS COMPOUNDS

[75] Inventors: Werner Ude, Darmstadt; Siegmund Besecke, Seeheim-Jugenheim; Achim Riemann, Marburg; Guenther Schroeder, Ober-Ramstadt, all of Fed. Rep. of Germany

[73] Assignee: Röhm GmbH, Darmstadt, Fed. Rep. of Germany

[21] Appl. No.: 751,625

[22] Filed: Jul. 2, 1985

[30] Foreign Application Priority Data

Jul. 10, 1984 [DE] Fed. Rep. of Germany ....... 3425282

[51] Int. Cl.$^4$ ................................................ C07F 9/53
[52] U.S. Cl. ........................................ 568/14; 568/15; 568/16; 568/17
[58] Field of Search ................... 568/16, 17, 14, 15

[56] References Cited

U.S. PATENT DOCUMENTS

| | | | |
|---|---|---|---|
| 2,138,835 | 12/1938 | Butz | 568/14 X |
| 2,902,517 | 9/1959 | Schmerling | 568/17 |
| 3,032,589 | 5/1962 | Hoffmann et al. | 568/14 X |
| 3,331,878 | 7/1967 | Priestley | 568/17 X |
| 3,450,772 | 6/1969 | Bridger et al. | 260/613 |
| 4,052,463 | 10/1977 | Uhing et al. | 568/14 |
| 4,087,408 | 5/1978 | Moedritzer | 568/15 X |
| 4,447,584 | 5/1984 | Bergeret et al. | 568/14 X |
| 4,463,159 | 7/1984 | Besecke et al. | 528/167 |
| 4,472,570 | 9/1984 | Besecke et al. | 528/167 |
| 4,492,805 | 1/1985 | Besecke et al. | 568/012 |

FOREIGN PATENT DOCUMENTS

| | | |
|---|---|---|
| 1238024 | 4/1967 | Fed. Rep. of Germany . |
| 3203186 | 8/1983 | Fed. Rep. of Germany . |
| 3231331 | 3/1984 | Fed. Rep. of Germany . |
| 1561198 | 2/1980 | United Kingdom . |

OTHER PUBLICATIONS

Kosolapoff et al, Organic Phosphorus Compounds, Wiley InterSc., N.Y., vol. 1, pp. 60 & 61 (1972).
Kosolapoff et al, Organic Phosphorus Compounds, Wiley InterSc., N.Y., vol. 3, pp. 379-383 (1972).
Kosolapoff et al, Organic Phosphorus Compounds, Wiley-InterSc., vol. 4, pp. 15, 16 and 44 (1972).
Chem. Abstr. 52, 20038a (1958).
Chem. Abstr. 87, 40281v (1977).
Chem. Abstr. 83, 43459n (1975).
Chem. Abstr. 96, 6000d (1982).
J. Org. Chem 42(12), 10 (1977).
Chem. Ber. 102 (9), 2922-2929 (1969).
Chem. Ber. 102 (9), 2914-2921 (1969).

*Primary Examiner*—Helen M. S. Sneed
*Attorney, Agent, or Firm*—Curtis, Morris & Safford

[57] ABSTRACT

Compounds of the formula

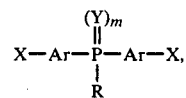

wherein R is lower alkyl or aryl, Y is oxygen or sulfur, m is 0 or 1, Ar is arylene, and X is halogen, methyl, or aryloxy, or polymers containing repeating units of this kind are prepared from a compound R—P(Y)$_r$Cl$_2$, where r is 0 or 1 but is never greater than m, by reaction with one or two molar parts of a compound H—ArX in the presence of a Friedel-Crafts catalyst.

2 Claims, No Drawings

METHOD FOR MAKING AROMATIC PHOSPHORUS COMPOUNDS

The present invention relates to methods for making certain aromatic phosphorus compounds, and to such compounds.

Phosphorus-containing polyarylene ethers having repeating units of the structure

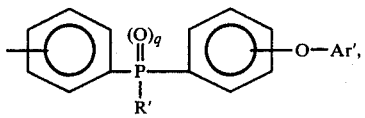

wherein R' is alkyl or aryl, Ar' is a bivalent aromatic group, and q is 0 or 1, are known from published German patent application DOS No. 32 03 186 as difficultly combustible or noncombustible plastics having resistance to high temperatures and a high softening temperature.

The present invention relates to a new method for making such polyarylene ethers or to monomeric starting compounds for such polyarylene ethers. The process involves a Friedel-Crafts reaction.

According to the aformentioned published German patent application, the polyarylene ethers there named are obtainable, for example, by the reaction of equimolar amounts of di(fluorophenyl)phenylphosphine oxide and of an aromatic diol such as dioxydiphenyl ether, with cleavage of hydrogen fluoride in the presence of a base. The di(fluorophenyl)phenylphosphine oxide and analogous starting compounds are prepared by reacting the Grignard reagent of a brominated aromatic hydrocarbon compound with dichlorophenylphosphine or dichlorophenylphosphine oxide in ether as the solvent, for example by the route

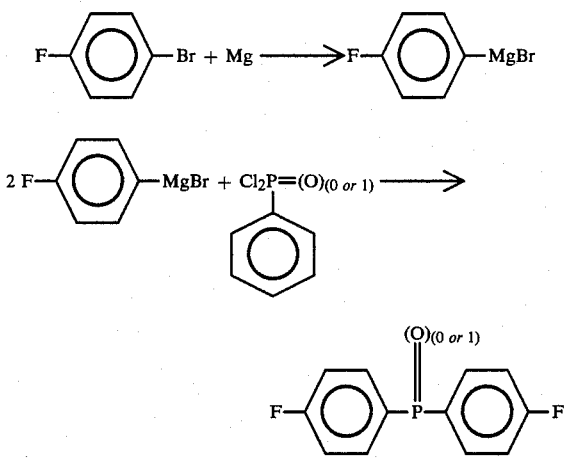

However, for a number of reasons the formation of a bond between the phosphorus atom and an aromatic nucleus by way of a Grignard reaction is not well suited for a commercial process, regardless of whether the latter is to be used directly for the production of polymers or for the preparation of monomeric starting materials therefor. Among these reasons are the necessity of using expensive bromine compounds, ether, and metallic magnesium, the high sensitivity of the reaction, the fire hazard due to the use of ether, and the risk that explosive peroxides may form.

It is further known to form an aromatic/phosphorus bond through a Friedel-Crafts reaction. Thus, V. V. Korschak (Isvestija Akademi Nauk USSR, Otdel, Chim. 1958, pp. 595–601) reacted para-chlorophenyldichlorophosphine with dibenzyl in the presence of aluminum chloride to give oligomeric compounds with repeating units of the structure

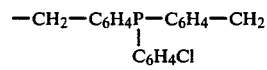

These oligomers do not have the desired polyether structure shown herein at the outset, nor are they suitable for use as intermediates in the preparation of such polyethers.

In published German patent application DAS No. 1,238,024, arylated phosphorus/thio compounds are prepared from trichlorophosphine sulfide or its derivatives in which one or two chlorine atoms are replaced by organic groups, and aromatic hydrocarbons in the presence of aluminum chloride or other Friedel-Crafts catalysts. The chlorine atoms contained in the chlorinated phosphine sulfide used are replaced by aromatic nuclei. However, this synthesis produces neither polymers nor starting materials from which phosphorus-containing polyarylene ethers can be obtained according to published German patent application DOS No. 32 03 188.

G. Olah and D. Hehemann (J. Org. Chem., Vol. 42, 1977, p. 2190) have found that phosphorus trichloride can be reacted in the presence of sulfur and of Friedel-Crafts catalysts with aromatic hydrocarbons to give good yields of triarylphosphine sulfides, which can be converted to the corresponding triarylphosphines by means of reducing agents.

The present inventors set themselves the task of preparing phosphorus-containing polyarylene ethers having the structure given earlier herein, or intermediates suitable for their preparation which contain a phosphorus atom bound to two aromatic nuclei and which can be converted by known processes to phosphorus-containing polyarylene ethers, in good yield from low-cost starting materials by a process which is technically readily controllable.

In a narrower sense, the object was to prepare in said advantageous manner compounds of the formula

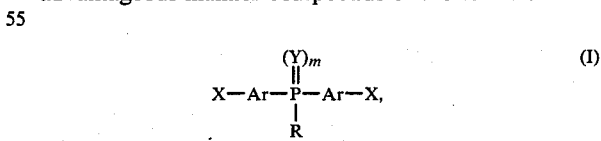

wherein R is lower alkyl or aryl, Y is oxygen or sulfur, m is 0 or 1, Ar is arylene, and X is halogen, methyl, or aryloxy. The compounds will be phosphorus-containing polyarylene ethers if X is an aryloxy group which in turn is linked to a further unit having the structure represented in the formula, as in polymers with repeating units of the structure

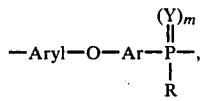

"Aryl" in this case symbolizes a bifunctional aromatic group which may be different from the group represented by Ar. For example, it may be a phenyl group or a polynuclear aromatic group having the structure

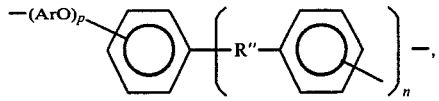

wherein R" is a covalent single bond, oxygen, sulfur, carbonyl, sulfonyl, methylene, or isopropylidene, or

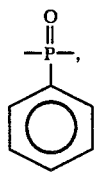

preferably oxygen or isopropylidene. Bridging groups R" free of hydrogen are preferred. n is an integer, at least 1 and generally not greater than 10, preferably 1 to 5. When n is greater than 1, the groups R" may be different. The terminal phenyl groups are preferably attached to an oxygen or sulfur atom or to a methylene or isopropylidene group. p is 0 or 1.

However, formula (I) may also represent intermediate products which can be converted into phosphorus-containing polyarylene ethers either directly or after further reaction. Moreover, some of the products so obtainable can also be converted to phosphorus-containing polyarylene esters, for example in accordance with published German patent applications DOS No. 32 31 331 or 32 22 571. When X is halogen, for example fluorine, the compounds

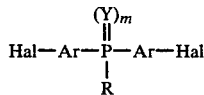

can be condensed with bisphenols to form polyarylene ethers. Compounds of formula (I) wherein X=CH$_3$ are converted by oxidation of the methyl group to the corresponding carboxylic acids:

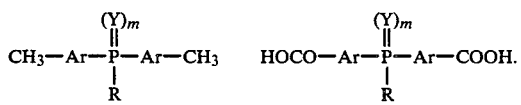

These can be reacted as such or in the form of their acid chlorides with bisphenols in accordance with published German patent application DOS No. 32 31 331 to yield phosphorus-containing polyarylene esters.

It has now been found that compounds of aforementioned formula (I) can be obtained in a simple manner in good yield by a readily controlled reaction from a compound R—P(Y)$_r$Cl$_2$, where r is 0 or 1 but is never greater than m, by reaction thereof with an aromatic compound of the formula H—ArX in the presence of a Friedel-Crafts catalyst. The compounds of formula (I) wherein m=1 and Y=sulfur are new substances which, when polymerized, form synthetic resins having valuable properties.

The phosphorus-containing starting compound R—P(Y)$_r$Cl$_2$ may, depending on the presence and nature of the group Y, be (A) a dichlorophosphine, R—PCl$_2$,
(B) a dichlorophosphine oxide, R—POCl$_2$, or
(C) a dichlorophosphine sulfide, R—PSCl$_2$.

The reactivity, and hence the preferability in the process of the invention, increases from dichlorophosphine oxide to dichlorophosphine to dichlorophosphine sulfide. The reactivity of dichlorophosphine (A) will correspond to that of dichlorophosphine sulfide (C) if the reaction is carried out in the presence of elemental sulfur, in which case a product of the formula (I) with a P=S bond (m=1, Y=S) is formed by sulfonation. The reactivity of dichlorophosphine oxide is markedly lower and satisfactory only for reaction with aromatic compounds of the formula H—Ar—O—Aryl to give polymeric products of the formula (I). For reaction with other aromatic compounds H—ArX, compounds of types (A) and (C) therefore are highly preferable.

The group R may be lower alkyl which as a rule contains not more than 4 carbon atoms. Methyl groups are preferred. R is preferably an aryl group, and more particularly an unsubstituted phenyl group.

Phosphine compounds of the types (A), (B) and (C) are known in the art and are obtainable by Friedel-Crafts arylation of the corresponding phosphorus trichlorides or by the reaction of such trichlorides with alkyl halides.

The aromatic compound H—ArX will usually contain a phenyl group unsubstituted in the ortho position or, preferably, in the para position. Although it may carry further substituents such as alkyl groups, alkoxy groups, halogen atoms, or nitro groups, unsubstituted phenyl groups are preferred. Polynuclear aromatic groups such as naphthylene groups are also suitable.

Among the substituents X, chlorine and fluorine are preferred. The most important examples of the compounds H—ArX are fluorobenzene and chlorobenzene. Further examples are toluene, and diphenyl ether. Although these compounds carry several hydrogen atoms on the aromatic nucleus, only one of these is usually replaced by a P—C bond in the Friedel-Crafts reaction.

When the process of the invention is to result directly in the formation of aromatic polyarylene ethers, a compound having at least two aromatic nuclei and at least one aromatic ether bond should be used as H—ArX. Diphenyl ether is the simplest examples of this group of substances. Further examples are polyethers of the structure C$_6$H$_6$—O—C$_6$H$_4$—O—C$_6$H$_5$ and bisphenyl ethers of bisphenols having the structure

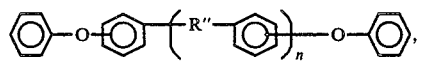

wherein R" and n may have the meanings given earlier. The bisphenyl ethers are obtainable from the corresponding bisphenols, for example through Ullmann coupling in accordance with U.S. Pat. No. 3,450,772.

The Friedel-Crafts reaction is carried out with so-called Friedel-Crafts catalysts, which are known per se (cf. Houben-Weyl, Vol. 7/20, pp. 15-19, and the literature there cited). In the main these are certain anhydrous metal halides such as tin tetrachloride, aluminum chloride, or iron chloride. Also, anhydrous zinc chloride and titanium tetrachloride can be used, although with a smaller yield. An electron gap in the metal atom is characteristic, on which the reactivity with the chlorine atoms of the dichlorophosphine compound is based. However, the Friedel-Crafts catalysts also include acids, such as polyphosphoric acid or sulfuric acid, or metals such as iron. Sulfonic acids of the formula U—$SO_3H$ can be employed, wherein U is $SbF_6$—, $CH_3$—, OH—, or $F(CF_2)_s$—, wherein s is zero or an integer from 1 to 8, particularly, 0, 1, 4, or 8. Anhydrous aluminum chloride is preferred. Like most other Friedel-Crafts catalysts, the catalyst of the present invention is used in a stoichiometric ratio of 1:1, or in an excess of up to 10:1, relative to the chlorine atoms of the phosphine chloride to be reacted. There are also Friedel-Crafts catalysts which are active in less than stoichiometric amounts.

The reaction is carried out in a nonaqueous polar medium. Carbon disulfide, nitrobenzene, and nitropropane are suitable, among others. Chlorobenzene or fluorobenzene can serve simultaneously as reactant and, when used in excess, as a reaction medium.

The quantitative ratio of the compounds R—P—$(Y)_r Cl_2$ and H—ArX will depend on the desired end product. To produce a high molecular weight polymer using a compound H—ArX which contains at least two aromatic nuclei, a molar ratio of exactly 1:1 is theoretically required. However, since a portion of the dichlorophosphine compound is consumed in side reactions, it is advantageous to use less than one mole of the aromatic compound H—ArX, for example from 0.9 to 0.95 mole per mole of the dichlorophosphine compound. When more than one mole of that compound is used, the oligomers formed will get progressively shorter as the amount increases.

The formation of monomeric compounds of the formula (I) stoichiometrically requires a molar ratio of 1:2, which, however, may be exceeded in favor of the aromatic compound in order to obtain complete conversion of the dichlorophosphine compound. Advantageous molar ratios range from 1:2 to 1:4.

The reaction proceeds at temperatures between 20° C. and 300° C., and preferably between 30° C. and 250° C., in from 0.5 to 120 hours. When dichlorophosphine sulfides or dichlorophosphines are used in the presence of elemental sulfur, temperatures or reaction times in the lower portion of the ranges indicated will suffice. The sulfur is advantageously used in an amount between 1 and 1.5 moles per mole of the dichlorophosphine compound. Under the conditions stated, yields ranging from 50 to about 90 percent, based on the dichlorophosphine compound used, can be obtained. As is customary in Friedel-Crafts processes, the reaction mixture is worked up by pouring it into ice water or concentrated hydrochloric acid, with the condensation product formed separating as an insoluble mass.

The preferred phosphorus-containing polyarylene ethers according to published German patent application DOS No. 32 03 186 contain the phosphorus in the form of phosphine oxide groups. With the process of the invention, these are formed directly only in the less preferred embodiment in which a dichlorophosphine oxide compound is used. The same holds true for the monomeric reaction products of formula (I). While compounds of the phosphine and phosphine sulfide types are more readily produced by the process of the invention than are compounds of the phosphine oxide type, they are less advantageous. Therefore, compounds of the phosphine type (m=0) or of the phosphine sulfide type (m=1, Y=S) obtained by the process of the invention from the corresponding starting compounds or in the presence of sulfur are preferably subsequently converted to the particularly stable compounds of the phosphine oxide type (m=1, Y=oxygen). This is done by subjecting the phosphine type compounds to the action of oxidants by known methods, and the compounds of the phosphine sulfide type to reaction with, e.g., dimethylsulfoxide or to hydrolysis, preferably under basic conditions. Also, trivalent phosphorus starting compounds may be oxidized during the synthesis to form pentavalent phosphorus compounds (r=0, m=1).

A better understanding of the present invention and of its many advantages will be had by referring to the following specific examples, given by way of illustration.

EXAMPLES 1 AND 2

63.3 g (0.3 mol) of phenylthiophosphonic acid dichloride, 213.6 g (1.6 mols) of anhydrous aluminum chloride, and 2 moles of chlorobenzene or fluorobenzene were heated to reflux for 8 hours in a one-liter four-necked flask equipped with stirrer, reflux condenser, and internal thermometer. On completion of the reaction, the reaction mixture was poured onto 500 ml of a mixture of ice and concentrated hydrochloric acid. The organic phase was separated. The aqueous phase was extracted four times with 300 ml portions of toluene. The combined organic phases were dried with sodium sulfate and evaporated in a rotary evaporator at 80° C. in a vacuum. The brownish residue obtained was distilled in an oil pump vacuum. After a forerun, an isomeric mixture of position-isomeric disubstituted triphenylphosphine sulfides consisting to the extent of at least 80% of the p,p'-disubstituted product distilled over at about 260° C. to 300° C. The remaining isomers were primarily o, p- or o, o'-, with traces of m, p-products.

| Example | Aromatic compound used | Dist. yield (g) | $P^{31}$—nmr signal* of principal product (δ) | Designation of product |
|---|---|---|---|---|
| 1 | Chlorobenzene | 97.3 | 42.55 | Dichlorophenyl-phenylphosphine sulfide |
| 2 | Fluorobenzene | 43.4 | 41.68 | Difluorophenyl-phenylphosphine sulfide |

*In $CDCl_3$ with $H_3PO_4$ capillary

EXAMPLE 3

1860 g (5.64 mols) of the 4,4'-difluorotriphenylphosphine sulfide made in Example 2 were introduced into a six liter flask equipped with a stirrer, thermometer, and distillation bridge attached to a receiver and two cold traps as well as a scrubber filled with concentrated potassium permanganate. 3375 ml of dimethylsulfoxide and 22.5 g of iodine were added with stirring. The reaction mixture was heated to 110° C. and the dimethylsulfide now formed as distilled off at 37°-40° C. vapor temperature. After eight hours of reaction, the development of dimethylsulfide ceased. 187.5 ml of 50% sulfuric acid were now added and the mixture was heated for a further six hours.

After conclusion of the reaction, the batch was filtered and the residue was washed with 500 ml of methylenechloride. The filtrate and methylenechloride wash were combined, concentrated in a rotation evaporator under a water jet vacuum to about 70% of the original volume, and then washed with sodium thiosulfate solution and subsequently with water. The organic phase was separated, dried with sodium sulfate, and subsequently distilled at about 1 Torr and at a distillation temperature of 230°–240° C. The solidified substance in the flask was, according to the $P^{31}$-nmr spectrum and GC/MS-measurement, about 96% 4,4'-difluorotriphenylphosphine oxide.

EXAMPLE 4

The same procedure was used as in Examples 1 and 2, except that toluene was used as the reactive aromatic compound in place of a halobenzene. Moreover, 100 ml of hexane were added to the reaction mixture and the amount of aluminum chloride was reduced to 1 mole. The product obtained after distillation was 8.1 g of crystals of an isomeric mixture of position-isomeric ditoluylphenylphosphine sulfides. $P^{31}$-nmr shift of principal component in $CDCl_3$ with $H_3PO_4$ capillary: $\delta = 43.20$ ppm.

EXAMPLES 5 AND 6

17.9 g (0.1 mol) of phenylphosphine dichloride, 3.2 g (0.1 mol) of sulfur, 0.2 g of anhydrous aluminum chloride, and 0.67 mol of chlorobenzene or fluorobenzene were stirred in a 250-ml four-necked flask equipped with stirrer, reflux condenser, internal thermometer, and off-gas line until the sulfur had gone into solution. 70.9 g (about 0.5 mol) of anhydrous aluminum chloride were then added. The reaction mixture was then heated to reflux for 8 hours. After cooling, the reaction mixture was gradually introduced into 500 ml of a mixture of concentrated hydrochloric acid and ice and then stirred for 1.5 hours at room temperature. The batch was then filtered to remove precipitated solids, the organic phase of the filtrate was separated, and the aqueous phase was extracted five times with 200 ml portions of toluene. The combined organic phases were dried with sodium sulfate and concentrated in a water jet vacuum at 70° C. The viscous residue was fractionally distilled in an oil pump vacuum. At about 260° C. to 300° C., an isomeric mixture of disubstituted triphenylphosphine sulfides distilled over.

| Example | Aromatic compound used | Dist. yield (g) | $P^{31}$—nmr signal* of principal product ($\delta$) | Designation of product |
|---|---|---|---|---|
| 5 | Chlorobenzene | 26.6 | 41.92 | Di(chlorophenyl)-phenylphosphine sulfide |
| 6 | Fluorobenzene | 20.7 | 41.75 | Di(fluorophenyl)-phenylphosphine sulfide |

*In $CDCl_3$ with $H_3PO_4$ capillary

EXAMPLES 7 AND 8

3.2 g (0.1 mol) of sulfur, 71.1 g (0.5 mol) of anhydrous aluminum chloride, and 0.5 mol of the aromatic compound indicated in the following table were introduced into a 250-ml four-necked flask equipped with stirrer, reflux condenser, dropping funnel, and internal thermometer. To this, a solution of 11.7 g (0.1 mol) of methylenephosphonic acid chloride in 0.4 mol of the aromatic compound was gradually added dropwise, with cooling.

The reaction mixture was then heated to reflux for the time reported in the table. The mixture was then introduced into 500 ml of a hydrochloride acid/ice mixture and stirred for 1.5 hours at room temperature. The mixture was filtered by suction and the organic phase was separated. The remaining aqueous phase was extracted five times with 200 ml portions of toluene. The combined organic phases were dried with $Na_2SO_4$ and the solvents were distilled off as much as possible in a water jet vacuum at about 70° C. The residue was fractionally distilled at about 0.2 millibar. The product distilled over at about 240° C. to 290° C.

| Example | Aromatic Compound used | Reaction Time (h) | Product (g) | $P^{31}$—nmr signal* of principal product ($\delta$) | Designation of product |
|---|---|---|---|---|---|
| 7 | Fluorobenzene | 24 | 19.7 | 42.05 | Di(fluorophenyl)-methylphosphine sulfide |
| 8 | Chlorobenzene | 8 | 21.8 | 41.51 | Di(chlorophenyl)-methylphosphine sulfide |

*In $CDCl_3$ with $H_3PO_4$ capillary

EXAMPLE 9

57.4 g (0.6 mol) of fluorobenzene and 17.9 g (0.1 mol) of dichlorophenylphosphine, 43.9 g (0.33 mol) of anhydrous aluminum chloride, and 32 mg of sulfur were heated to about 200° C. in an 0.35 liter Roth autoclave with a Hastelloy C lining, magnetic plunger, and electric heating. The internal temperature rose temporarily to 220° C. as a result of the initially apparently markedly exothermic reaction. The reaction mixture was held at 200° C. for 2 hours. At the end of that time it was cooled to room temperature and the pressure in the autoclave was relieved. The reaction solution was rinsed with 250 ml of toluene in a flask, mixed with 26 g of KCl and stirred for 30 minutes at 90° C. After the batch had cooled to room temperature, it was introduced with ice water cooling into 250 ml of 10% hydrochloric acid, then washed with a little water and stirred for 60 minutes at room temperature. It was then filtered and the remaining solid substance was washed with a total of 800 ml of dichloromethane.

The organic phase of the filtrate was separated and the aqueous phase washed four times with 300 ml portions of methylene chloride. The combined organic phases were dried with $Na_2SO_4$, the solvent was evaporated as much as possible in a rotary evaporator at 60° C., and the residue was fractionally distilled in an oil-pump vacuum. 12 g of a brownish, highly viscous distillate consisting largely of difluorotriphenylphosphine oxides was obtained.

| | Microanalysis: | | |
|---|---|---|---|
| | C | H | P |
| Theor. | 70.7 | 4.5 | 9.4 |
| Found | 71.1 | 5.1 | 9.3 |

$P^{31}$ chemical shift of principal product: $\delta = 29.20$

EXAMPLES 10 TO 12

35.2 g (0.1 mol) of 4,4'-di(phenoxy)diphenyl ether ($C_6H_5OC_6H_4OC_6H_4OC_6H_5$), 21.1 g (0.1 mol) of phenylthiophosphonic acid dichloride, and 0.5 mol of one of the Lewis acids listed in the following table were introduced into a 250 ml four-necked flask equipped with a KPG borosilicate glass stirrer, thermometer, condenser, gas inlet pipe, and off-gas line. The mixture was heated to 150° C. while nitrogen was being introduced, with the contents of the flask becoming increasingly viscous. The batch was held at 150° C. for a total of 6 hours, after which 37.2 g of potassium chloride were added and the mixture was again stirred for 15 minutes at 120° C. The contents of the flask were then poured into 3 liters of distilled water. The partly flocculent product was filtered off by suction and distilled as much as possible in about 300 ml of tetrahydrofuran with stirring. This solution was filtered and gradually added dropwise to 3 liters of distilled water. The precipitate so obtained was filtered off by suction and washed on the filter with water. The polymeric product formed was then dried to constant weight at 60° C. in a vacuum.

| Example | Catalyst | Catalyst Amount (g) | Yield (%) | Reduced Viscosity (dl/g) Measured in $CHCl_3$ |
| --- | --- | --- | --- | --- |
| 10 | $AlCl_3$ | 66.8 | 36 | 0.3 |
| 11 | $FeCl_3$ | 81.2 | 6 | 0.2 |
| 12 | $SnCl_3$ | 55.9 | 54.3 | 0.1 |

EXAMPLE 13

17 g (0.1 mol) of diphenyl ether, 19.5 g (0.1 mol) of phenylphosphonic acid dichloride ($C_6H_5$—$POCl_2$), and 5.4 g (0.033 mol) of anhydrous ferric chloride were heated to 215° C. with stirring under a weak argon stream in a 100 ml four necked round bottomed flask equipped with a blade type stirrer of KPG borosilicate glass, thermometer, condenser, and argon connection. After a reaction time of 15 hours at 215° C. to 220° C., the reaction mixture was cooled and stirred into a mixture of 700 ml of 2-propanol and 200 ml of water. The solid substance was filtered off by suction and washed three times with 100 ml portions of petroleum ether. 18.9 g of a polycondensate soluble in dimethyl formamide were obtained, which product could again be precipitated in water.

P content: Theor. 10.6, found 10.1.

EXAMPLE 14

17 g (0.1 mol) of diphenyl ether, 17.9 g of phenylphosphonous acid dichloride ($C_6H_5PCl_2$), and 10 mol percent of anhydrous ferric chloride (based on the $C_6H_5PCl_2$) were heated in 100 ml of nitrobenzene to 200° C. over 2 hours in a 250-ml four necked round bottomed flask equipped with a blade type stirrer of KPG borosilicate glass, thermometer, condenser, and argon connection. The cooled reaction mixture was stirred into a mixture of 1.4 liters of isopropanol and 500 ml of water. The solid substance was filtered off by suction and washed three times with 100 ml portions of isopropanol. It was possible to dissolve the product in DMF and then again precipitate it in water. 12.9 g of a polycondensate were so obtained. A cast sheet could be produced from a solution thereof in chloroform. The reduced viscosity of the chloroform solution of the product was about 0.2 dl/g.

EXAMPLE 15

17 g (0.1 mmol) of diphenyl ether, 21.1 g (0.1 mol) of phenylthiophosphonic acid dichloride, and 0.25 mol of anhydrous aluminum chloride were introduced into a 250 ml four necked flask equipped with a KPG borosilicate glass stirrer, thermometer, condenser, gas inlet pipe, and off-gas line. The mixture was heated to 150° C. while nitrogen was being introduced.

The mixture was held at 150° C. for a total of 6 hours. At the end of that time, 37.2 g of potassium chloride were added and the mixture was stirred for another 15 minutes at 120° C. The product obtained was poured into 3 liters of distilled water and the precipitate formed was filtered off with suction. After the filtration residue had been washed with water, the product was dissolved in DMF and again precipitated in water. After drying to constant weight at 60° C. in a vacuum, 10 g of a polycondensate were obtained. A cast sheet could be produced from a solution of the product in chloroform.

P content: Theor. 10.0, found 10.5.

EXAMPLE 16

17.9 g (0.1 mol) of phenylphosphine dichloride 3.2 g (0.1 mol) of elemental sulfur, 100 ml nitrobenzene, 1 g of anhydrous aluminum chloride, and 17 g (0.1 mol) of diphenyl ether were stirred together for about 1 hour at 40° C. in a 250 ml four necked flask equipped with a stirrer, thermometer, reflux condenser, and argon connection. After the introduction of a further 70 g of anhydrous aluminum chloride, the mixture was warmed for 19 hours at 40° C.

The cooled reaction mixture was slowly dropped into 2.5 liters of water. The precipitated solid substance which formed was vacuum filtered and washed three times with 100 ml portions of isopropanol. The filter residue was stirred for four hours with 500 ml of concentrated hydrochloric acid at the boiling temperature. After cooling, the insoluble product was separated by filtration, washed thoroughly with water and isopropanol, and the residue was dried to constant weight at 80° C. in vacuum. 15 g of polycondensate were obtained. The reduced viscosity, $\eta_{sp}/c$, of a chloroform solution of the product was about 0.2 dl/g.

EXAMPLE 17

204 g (1.2 mol) of diphenylether and 133.4 g (1.0 mol) of anhydrous aluminum chloride were introduced into a one liter four necked flask equipped with a stirrer, thermometer, condenser and calcium chloride tube. Subsequently, 63.3 g of phenylthiophosphonic acid dichloride (0.3 mol) were added dropwise over a period of about five minutes. The mixture was now slowly heated to 130° C. and maintained at this temperature while stirring until no further evolution of hydrogen chloride could be detected (about 6 hours). The batch was permitted to cool somewhat and then was introduced in portions into 4 liters of a mixture of equal parts of ice and dilute hydrochloric acid. After standing for 18 hours at room temperature, this acid mixture was extracted with five 500 ml portions of methylenechloride. The organic phase was then washed with water and subsequently dried with over sodium sulfate. After concentration in a water jet vacuum at 30° C., 160 g of a dark mass are obtained which, according to $C^{13}$- and P³¹-nmr spectra, contained more than 90% of 4,4'-diphenoxytriphenyl-phosphine sulfide.

EXAMPLE 18

12.1 g of 4,4'-diphenoxydiphenylsulfone were stirred for fifteen minutes at room temperature with trifluoromethane sulfonic acid in a 100 ml flask equipped with a stirrer, thermometer, and a reflux condenser equipped with a scrubber containing NaOH solution. Then, while argon was introduced, 4.2 ml of dichlorophenylphosphine oxide were introduced over a period of 10 minutes, whereby an exothermic reaction raising the temperature to 46° C. was observed. After heating to 100° C., the batch was stirred at this temperature for 26 hours. For completion of the reaction, the mixture was maintained for a further 70 hours at 100° C. After cooling, the batch was combined with 600 ml of water. The solid substance formed was vacuum filtered and washed to neutrality on the filter. The dark reaction product was washed twice with methanol. The moist product was dissolved in 60 ml of dichloromethane and the solution was filtered. The filtrate was introduced dropwise into 600 ml of cyclohexane. A product precipitated which was separated from the remaining solution by decantation and the residue was washed three times with petroleum ether. Finally, the brown powder formed was dried at 60° C. to constant weight in a vacuum. Yield: 12.1 g (76.9% of theory).

The product forms a brittle cast film from chloroform.

If the equivalent amount of fluorosulfonic acid or of perfluorinated butane sulfonic acid or octane sulfonic acid are employed instead of trifluoromethane sulfonic acid, substantially the same result is obtained.

In the same manner the condensation proceeds with 4,4'-diphenoxydiphenyl ether, 4,4'-diphenoxydiphenyl sulfide, 4,4'-diphenoxybenzophenone, or 4,4'-diphenoxytriphenyl phosphine oxide instead of diphenoxydiphenylsulfone. Polycondensates are obtained which form cast films from chloroform solution.

EXAMPLE 19

The same procedure was used as in Example 18, except that 2,2-diphenylpropane (19.6 g) and phenylthiophosphonic acid dichloride (21.1 g) were used as reactants. The reaction product was a yellow powder. Yield: 19 g (51% of theory).

The product forms a brittle film when cast from chloroform.

What is claimed is:

1. A method for making an aromatic phosphorus compound of the formula

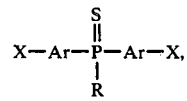

wherein R is methyl or phenyl, Ar is phenylene, and X is chlorine or fluorine, and at least 80 percent of said compound is present as the p,p'-isomer, which method comprises reacting one molar part of a compound R—PCl₂ with at least two molar parts of a compound H—ArX in the presence of at least one molar part of elemental sulfur, and of a Friedel-Crafts catalyst.

2. A method as in claim 1 wherein said catalyst is an anhydrous chloride of aluminum, iron, tin, zinc, or titanium or is a sulfonic acid of the formula U—SO₃H, where U— is SbF₆—, CH₃—, HO—, or F(CF₂)ₛ— where s is zero or an integer from 1 to 8.

* * * * *